United States Patent [19]

Arndts et al.

[11] Patent Number: 4,871,760

[45] Date of Patent: Oct. 3, 1989

[54] USE OF 2-(N-2,6-DICHLOROPHENYL-N-ALLYLAMINO)-2-IMIDAZOLINE AS CYTOPROTECTIVE AGENT

[75] Inventors: Dietrich Arndts, Appenheim; Günter Schingnitz, Bad Kreuznach; Ilse Streller, Stromberg; Alexander Walland, Ingelheim am Rhein, all of Fed. Rep. of Germany

[73] Assignee: Boehringer Ingelheim KG, Ingelheim am Rhein, Fed. Rep. of Germany

[21] Appl. No.: 63,617

[22] Filed: Jun. 18, 1987

[30] Foreign Application Priority Data

Jun. 18, 1986 [DE] Fed. Rep. of Germany ....... 3620433

[51] Int. Cl.⁴ .......................................... A61K 31/415
[52] U.S. Cl. ..................................................... 514/401
[58] Field of Search .......................................... 514/401

[56] References Cited

PUBLICATIONS

Chem. Abst. 45754x (1982).

*Primary Examiner*—Stanley J. Friedman
*Attorney, Agent, or Firm*—David E. Frankhouser; Alan R. Stempel; Mary-Ellen M. Timbers

[57] ABSTRACT

The invention relates to the use of 2-[N-(2,6-dichlorophenyl)-N-allylamino]-2-imidazoline as a cytoprotective agent.

1 Claim, No Drawings

USE OF 2-(N-2,6-DICHLOROPHENYL-N-ALLYLAMINO)-2-IMIDAZOLINE AS CYTOPROTECTIVE AGENT

The invention relates to the use of 2-[N-2,6-dichlorophenyl-N-allylamino]-2-imidazoline and its acid addition salts as agents for cytoprotection.

It is known that 2-[N-2,6-dichlorophenyl-N-allylamino]-2-imidazoline and its acid addition salts have valuable pharmacological properties. The compound, its preparation and processing to forms for pharmaceutical use are described in German Offenlegungsschrift No. 19 58 201, the analgesic Properties of the compounds disclosed in this Offenlegungsschrift being emphasised. German Offenlegungsschrift No. 28 31 190 (U.S. Pat. No. 4,271,175) discloses the use of 2-[N-2,6-dichlorophenyl-N-allylamino]-2-imidazoline and its acid addition salts as bradycardic agents. The compound is also known in the literature under the name alinidine.

It has now been found, surprisingly, that 2-[N-2,6-dichlorophenyl-N-allylamino]-2-imidazoline, as well as its acid addition salts, has a cytoprotective action.

The cytoprotective action of alinidine was investigated on the isolated rat heart under conditions of ischaemia with subsequent reperfusion (retrograde perfusion via the aorta by the Langendorff method) and after perfusion with calcium-free and then calcium-containing solution (calcium paradox, Ruigrok et al., Europ. J. Cardiol. 3, 59, 1975).

Male rats (Chbb:Thom) were killed by a blow to the neck, and the heart was rapidly removed and perfused by the Langendorff method under constant pressure (80 cm $H_2O$). The pressure developed in the left ventricle was measured using a liquid-filled balloon catheter and, in experiments on the calcium paradox, spontaneous heart rate was also determined from the pressure plots.

In the case of 30 hearts, the right atrium was removed and the heart was electrically stimulated at the frequency of 300/min (pulse duration 1 msec) with a bipolar electrode inserted into the right ventricle. After an equilibration period lasting 10 minutes, alinidine (3 concentrations, n=6 for each), dissolved in ungassed perfusion medium or, in control experiments (n=12), the medium alone, was infused by (1 ml/min) into the perfusion system by means of an infusion pump near the heart. 10 min thereafter the ischaemia period was started, with the flow rate reduced by a factor of 100 and the infusion rate reduced to 0.1 ml/min. The ischaemia lasted 60 min and was followed by reperfusion with the normal flow rate and termination of the infusion. The heart action ceases 1–2 min after the change to ischaemia. Reperfusion brings about a large increase in the basic tension, and the heart action resumes after a mean of 6.8 min, initially irregularly, and after 17 min there is a rapid transition to contractions synchronous with the stimulae.

Alinidine brought about a reduction in the duration of an irregular heart action on reperfusion, which depended on the concentration in the ischaemia period (6.6, 13.3 and 33.3 $\mu$/ml). After 13.3 and 33.3 $\mu$/ml, the figures differed significantly by 4.4 and 5.4 min from the control figures (17 min).

42 hearts were, after a 20-minute equilibration period, perfused with a calcium-free NaEDTA-containing solution for 30 min, and were then reperfused with normal solution for 3 min. After the end of the experiment, the wet weight of the hearts was determined, and, after drying and leaching out with 0.1 N HCl, the sodium and potassium contents were determined by atomic absorption spectrophotometry. The perfusate was collected in 3-min periods, measured and the content of creatine phosphokinase (CPK), lactate dehydrogenase (LDH) and glutamate-oxaloacetate trans-aminase (GOT) were determined with an automatic analyser. Perfusion with calcium-free solution causes the heart action to cease after 1–2 min, and there is pronounced contracture on reperfusion. The enzyme outputs in the equilibration period were 0.65±0.083 U/g.min CPK, 0.55±0.073 U/g.min LDH and 0.1±0.09 U/g.min GOT. The enzyme outputs rose by 22-to 27-fold during reperfusion.

Addition of 16 $\mu$/ml alinidine to all the perfusion solutions reduced the heart rate in the equilibration Period significantly to 118 beats/min compared with 184 beats/min in the control group (n was 21 in each group). The enzyme losses were significantly reduced by alinidine compared with the control group. Calculation of the enzyme output in U/g heart.min produced the following figures: CPK: reduction from 18.8 to 7.3; LDH: reduction from 12.2 to 5.7; GOT: reduction from 2.4 to 0.8. There was likewise a significant effect of alinidine on the electrolyte content of the hearts. The sodium content was 835 $\mu$/g heart and the potassium content was 1377 $\mu$/g heart in the control group, while 648 and 1809 $\mu$/g heart, respectively, were measured in the alinidine group.

The results show a diminution in the cell damage after ischaemia/reperfusion and in the calcium paradox. The reduction in the hazardous initial period after reperfusion in ischaemia experiments and the diminution in the enzyme loss in the calcium paradox expression of a cytoprotective action which is independent of the heart rate.

The myocardial $^{45}Ca$ content as a measure of the cytoprotection:

Sympathomimetic stimulation of conscious rats with high isoprenaline doses induces disseminated myocardial necroses. The morphology and pathophysiology of this tissue damage substantially correlate with those of ischaemia-related myocardial necroses (A. Fleckenstein et al. in "Calcium Entry Blockers and Tissue Protection", ed. by T. Godfraind et al., Raven Press, New York, 1985). The intensity of the cardiac necrosis correlates with the massive $Ca^{++}$ influx into the myocardium. When a radioactive indicator ($^{45}CaCl_2$) is used simultaneously, the amount of the myocardial radioactivity is very reliable and an easily quantifiable measure of the cardiac lesion. Cytoprotective active substances dose-dependently inhibit the isoprenaline-related monocardial necroses. Thus, using a method described by D. Arndts (Arzneimittelforsch. 25: 1279-1284, 1975) the cytoprotective effects of oral doses of alinidine were investigated on a total of 36 conscious rats.

All the animals received an i.p. injection of 10 $\mu$Ci/kg body weight $^{45}CaCl_2$. In addition to two control groups (N=6 in each), which received either only physiol. saline solution or 30 mg/kg isoprenaline s.c., the remaining 4 animal groups (N=6 in each) received, in addition to isoprenaline (30 mg/kg), increasing doses of alinidine orally (10 mg/kg, 3 mg/kg, 1 mg/kg and 0.3 mg/kg). After exactly 6 hours, the animals were lightly anaesthetised with diethyl ether and thoracotamised. After blood had been removed from the right atrium of the heart, the hearts were removed and about 50 mg of the right ventricle was dissected out and lysed in SOLUENE ®. The radioactivity in the blood plasma and the solubilised myocardium was quantified by liquid scintillation spectrometry. The myocardial radioactivity was calculated as a percentage of the plasma radioactivity per g of tissue. The oral dose of alinidine which inhibited the isoprenaline-related myocardial radiocalcium uptake by 50% was determined. This figure, which is called the $H_{50}$ value, was 1.6 mg/kg for alinidine. This dose having a cytoprotective action is in the same range as that of the comparison substances verapamil or metoprolol but without having the side effects of a calcium antagonist or β-blocker.

Action of alinidine in the hypoxia tolerance test

The hypoxia tolerance test is basically carried out by the following method (Hoffmeister et al., 1982*): A group of 10 mice (neutered, ChbI: NMRI) receives the particular dose of the test substance administered 3 times, namely 24 h, 16 h and 30 min before the start of the actual test. At the same time, a further 10 animals, which act as controls, receive the vehicle without the test substance. To test the hypoxia tolerance, the animals which have thus been pretreated (substance group and control group) are each Placed in one half of a transparent perspex chamber which is divided in the middle by a partition.

After 2 min have elapsed, the chamber is closed airtight, and a gas mixture composed of 96.5% $N_2$ and 3.5% $O_2$ is passed through (12 min). The first animals die 6-7 min later. When only 2-3 of the 10 animals in the control group still show signs of life, the gas flow is terminated and the lid is open. Without touching the animals, a further 15 min is allowed to elapse, and then the number of surviving animals in the substance and control groups is finally determined.

In the present experiments, alinidine was injected subcutaneously in physiological NaCl solution, and the control animals received s.c. injections of NaCl solution.

*Hofmeister, F.; Benz. U.; Heise, A.; Krause, V.; Neuser, H. P., Behavioral Effects of Nimodipine in Animals, Arzneim.-Forsch./Drup Research 32 (I), 347–360 (1982).

As a departure from the general scheme, in the experiments with intracerebral administration only a single dose of alinidine, likewise in NaCl solution, was administered half an hour before the start of the experiment. Accordingly, the control animals in these experiments also received only a single intracerebral injection of an NaCl solution.

The results show that hypoxia tolerances improved on pretreatment with alinidine.

1 Effect on the calcium ion kinetics on rabbit aortic strips

Methode according to that described by C. Van Breemen, P. Aaronson, R. loutzenheiser, K. Meisheri Chest 78:157s–165s, 1980
R. Casteels & G. Drogman
J. Physiol 317: 263 270, 1981

$^{45}Ca^{2+}$ loaded aortic strips were equilibrated in physiological salt solution. The efflux rate is estimated. After stimulation by addition of 80 mM K+ the efflux rate is increased. Result: Alinidine potentiates the $Ca^{2+}$-efflux by 40% after stimulation with 80 mM K+. That means possibly an activation of the $Ca^{2+}$- pump.

2. Effect on the Na+K+- pump on human red blood cells.

Methode as described by J. Duhm & B. O. Gobel Am J Physiol, 15: C20–C29, 1984

The pump activity is measured as ouabain sensitive Rb+ influx

Result: Alinidine increases the pump activity also in the presence of ouabain. That means that the inhibitory effect of ouabain is abolished.

3. Effect on Na+-K+- cotransport system on human red blood cells

Methode after M. Canessa, A. Adragna, H. S. Solomon, T. M. Conolly, D. C. Toesteson N Engl J Med 302: 772–776, 1980

RBC (Red Blood Cells) were loaded with Na+ to stimulate the activity of the cotransport system maximally. The furosemide sensitive part of the Na+ and K+- efflux is estimated which is a measure of the contransport system.

Result: Alinidine increases selectivity the Na+- efflux four times while the K+- efflux remains the same.

Thus Alinidine increases the Na+- efflux from RBC's without effecting the K+- efflux.

On the basis of these findings, the compounds described here, and their acid addition salts, ought to find use as active substance for medicaments having a cytoprotective action.

They can be used according to the invention as a cytoprotective for the therapy or prophylaxis of the indications which are listed hereinafter:

Cytoprotection during stress, especially due to hypoxia; prevention of disseminated necrosis in the course of coronary heart disease and cardiac insufficiency, cerebral metabolic disturbances, organic brain syndrome, cerebral oxygen deficiency, treatment of cerebral sclerosis, cerebral apoplexy, cell damage resulting from drug abuse, especially due to alcoholism.

The compounds can be administered both enterally and parenterally. The proposed single dose is 1 to 50 mg of active substance. The desired dose depends on the indication and presentation and can be determined by experiment.

Examples of forms suitable for use are tablets, capsules, suppositories, solutions, syrups, emulsions, aerosols or dispersible powders. Appropriate tablets can be obtained by, for example, mixing the active substance with known auxiliaries, for example inert diluents, such as calcium carbonate, calcium phosphate or lactose, disintegrants, such as maize starch or alginic acid, binders, such as starch or gelatine, lubricants, such as magnesium stearate or talc and/or agents to achieve a depot effect, such as carboxypolymethylene, carboxymethylene cellulose, cellulose acetate phthalate or polyvinyl acetate. The tablets can also be composed of several layers.

Correspondingly, coated tablets can be prepared by coating cores, which have been prepared analogously to the tablets, with agents customarily used in tablet coatings, for example collidone or schellack, gum arabic, talc, titanium dioxide or sugar. It is also possible for the core to be composed of several layers to achieve a depot effect or to avoid incompatibilities. Likewise, it is also possible for the tablet coating to be composed of several layers, to achieve a depot effect, it being possible to use the auxiliaries mentioned above for the tablets.

Syrups of the active substances, or combinations of active substances, according to the invention can also contain a sweetener, such as saccharin, cyclamate, glycerol or sugar as well as a flavour improver, for example flavourings such as vanillin or orange extract. They can also contain suspending auxiliaries or thickening agents, such as sodium carboxymethylcellulose, wetting agents, for example condensation products of fatty alcohols with ethylene oxide, or protectives, such as p-hydroxybenzoates.

Injection solutions are prepared in the customary manner, for example with the addition of preservatives, such as p-hydroxybenzoates, or stabilisers, such as alkali metal salts of ethylenediaminetetraacetic acid, and dispensed into injection vials or ampoules.

The capsules containing one or more active substances, or combinations of active substances, can be prepared by, for example, mixing the active substances with inert excipients, such as lactose or sorbitol, and encapsulating in gelatin capsules.

Suitable suppositories can be prepared, for example, by mixing with vehicles intended for this purpose, such as neutral fats or polyethylene glycol or its derivatives.

EXAMPLES

Example of the preparation of the active substance 2-[N-(2,6-Dichlorophenyl)-N-allylamino]-2-imidazoline 2.0 g of 2-(2,6-Dichlorophenylamino)-2-imidazoline are heated together with 3 ml of allyl bromide and 1 ml of pyridine in 10 ccm of absolute methanol in a tube at 100° C. for about 15 hours. The reaction mixture is then evaporated to dryness in vacuo, and the remaining residue is dissolved in a little dilute hydrochloric acid. For its purification, the solution in hydrochloric acid is extracted with ether, and the ether extracts are discarded. The oily imidazoline base is then liberated with 5 N sodium hydroxide solution and crystallises after cooling in ice for some time. It is filtered off with suction, washed with distilled water and dried. The yield is 1.5 g, which is 83.8% of theory.

Melting point 130°–131° C. The nitrate prepared in the customary way melts at 136°–138° C.

Other acid addition salts can be prepared by known processes.

EXAMPLE A

Tablets

| | |
|---|---|
| 2-[N—2,6-Dichlorophenyl-N—allylamino]-2-imidazoline.HBr | 10 mg |
| Lactose | 65 mg |
| | 125 mg |
| sec.calcium phosphate | 40 mg |
| Soluble starch | 3 mg |
| Magnesium stearate | 3 mg |
| Colloidal silica | 4 mg |
| total | 250 mg |

Preparation

The active substance is mixed with a portion of the auxiliaries, and the mixture is vigorously kneaded with an aqueous solution of the soluble starch and granulated in the customary manner using a screen. The granules are mixed with the remainder of the auxiliaries, and the mixture is compressed to form tablet cores weighing 250 mg which are then coated in the customary manner using sugar, talc and gum arabic.

EXAMPLE B

Ampoules

| | |
|---|---|
| 2-[N—2,6-Dichlorophenyl-N—allylamino]-2-imidazoline.HBr | 1.0 mg |
| Sodium chloride | 18.0 mg |
| Distilled water ad | 2.0 ml |

Preparation

The active substance and sodium chloride are dissolved in water, and the solution is dispensed into glass ampoules under nitrogen.

Example C

Drops

| | |
|---|---|
| 2-[N—2,6-Dichlorophenyl-N—allylamino]-2-imidazoline.HBr | 0.02 g |
| Methyl p-hydroxybenzoate | 0.07 g |
| Propyl p-hydroxybenzoate | 0.03 g |
| Demineralised water ad | 100 ml |

What is claimed is:

1. A method for treating cerebral brain disturbances, cerebral oxygen deficiency, cerebral sclerosis or cerebral apoplexy which method compromises administering to an animal suffering from one of the said conditions a therapeutically effective amount of 2-[N-2,6-dichlorophenyl-N-allylamino]-2- imidazoline or a pharmaceutically acceptable acid addition salt thereof.

* * * * *